(12) United States Patent
Douglas et al.

(10) Patent No.: US 10,517,546 B2
(45) Date of Patent: *Dec. 31, 2019

(54) SPATIAL RESOLUTION IN MOLECULAR AND RADIOLOGICAL IMAGING

(71) Applicants: David Byron Douglas, Winter Park, FL (US); Robert E. Douglas, Winter Park, FL (US)

(72) Inventors: David Byron Douglas, Winter Park, FL (US); Robert E. Douglas, Winter Park, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/016,716

(22) Filed: Jun. 25, 2018

(65) Prior Publication Data

US 2018/0303439 A1    Oct. 25, 2018

Related U.S. Application Data

(62) Division of application No. 14/644,489, filed on Mar. 11, 2015, now Pat. No. 10,034,640.

(51) Int. Cl.
  *G01T 1/29* (2006.01)
  *A61B 6/03* (2006.01)
  *A61B 6/00* (2006.01)
  *A61B 6/06* (2006.01)

(52) U.S. Cl.
  CPC ............ *A61B 6/037* (2013.01); *A61B 6/032* (2013.01); *A61B 6/4291* (2013.01); *A61B 6/4417* (2013.01); *A61B 6/5282* (2013.01); *G01T 1/2985* (2013.01); *A61B 6/06* (2013.01); *A61B 6/5205* (2013.01)

(58) Field of Classification Search
  CPC ....... G01T 1/204; G01T 1/2045; G01T 1/202; G01T 1/178; G01T 1/2985
  See application file for complete search history.

(56) References Cited

U.S. PATENT DOCUMENTS

| | | | | |
|---|---|---|---|---|
| 6,100,531 A | * | 8/2000 | Hines | .................... G01T 1/1642 250/363.04 |
| 2007/0242806 A1 | * | 10/2007 | Borgmann | ............... A61B 6/08 378/207 |
| 2008/0128631 A1 | * | 6/2008 | Suhami | ..................... G01T 5/02 250/370.09 |
| 2008/0180580 A1 | * | 7/2008 | Kadrmas | ............... G06T 11/003 348/744 |

(Continued)

*Primary Examiner* — David P Porta
*Assistant Examiner* — Mamadou Faye
(74) *Attorney, Agent, or Firm* — Anderson Gorecki LLP

(57) ABSTRACT

A method and apparatus for improvement of spatial resolution in molecular and radiological imaging is presented. System equipment includes bed with either flat or cylindrical detectors large detector arrays with collimator(s), lens(s), mirror(s) and/or shutter(s). This system utilizes magnification principles with large detector arrays. There is error reduction by reduction of non-collinearity error as seen in current PET scans by determination of the trajectory of the photons and accurate localization of the annihilation event of a positron. Additional error reduction of random coincidence and scatter coincidence is seen. Overall, this method and apparatus affords improved spatial resolution and higher efficiencies, which would allow for lower cost and dose reduction to the patient.

1 Claim, 15 Drawing Sheets

(56) References Cited

U.S. PATENT DOCUMENTS

| | | | |
|---|---|---|---|
| 2009/0116720 A1* | 5/2009 | Ritman | A61B 6/00 |
| | | | 382/132 |
| 2010/0108896 A1* | 5/2010 | Surti | G01T 1/00 |
| | | | 250/363.04 |
| 2010/0316189 A1* | 12/2010 | Davis | G01N 23/04 |
| | | | 378/62 |
| 2011/0080994 A1* | 4/2011 | Hoffman | A61B 6/032 |
| | | | 378/19 |
| 2013/0102830 A1* | 4/2013 | Otto | A61N 5/1031 |
| | | | 600/1 |

* cited by examiner

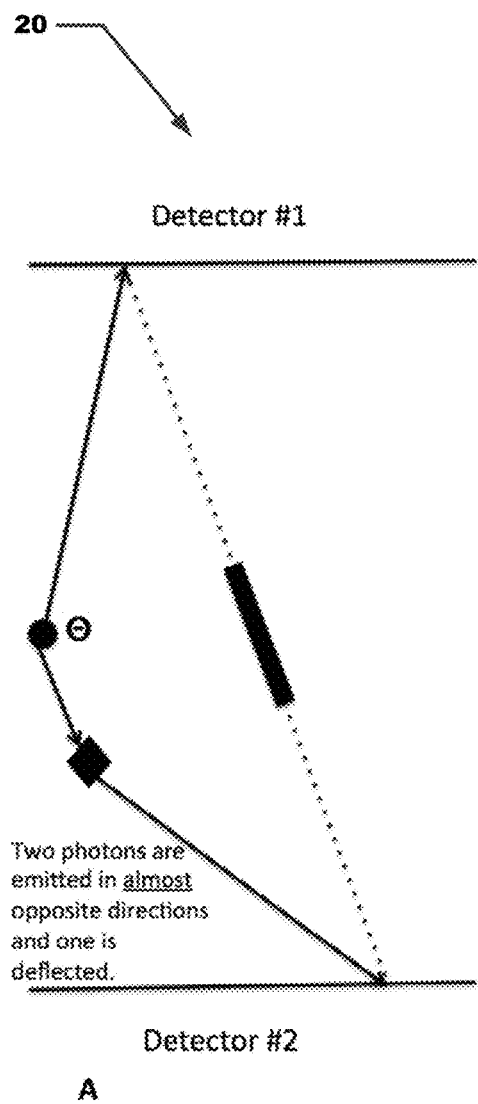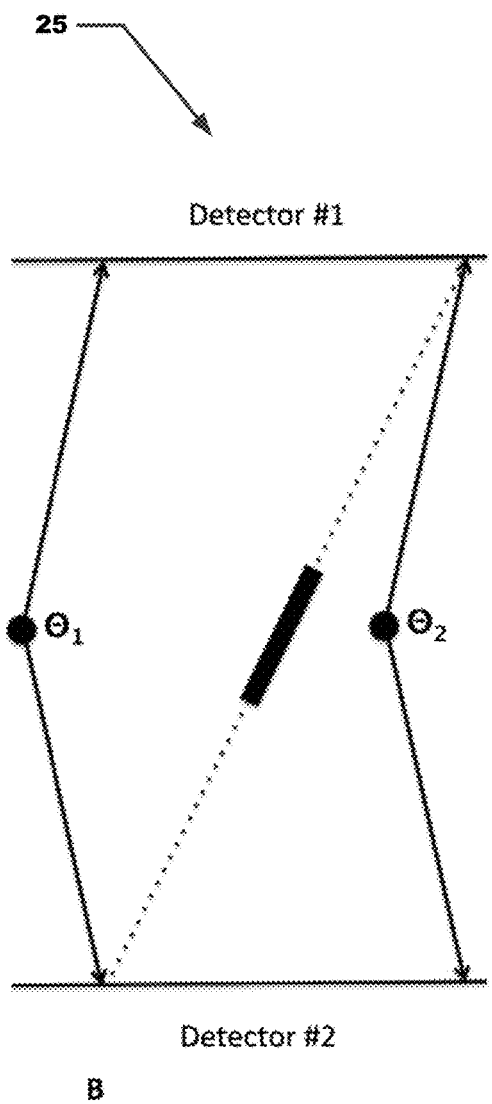
*FIGURE 2A*  *FIGURE 2B*

A B

SPATIAL RESOLUTION IN MOLECULAR AND RADIOLOGICAL IMAGING

BACKGROUND

A gamma camera is a system used in the medical subspecialty of nuclear medicine. The gamma camera has the ability to detect photons from radionuclide or radiopharmaceutical. The radiopharmaceutical is administered into the body and it will then distribute in accordance with body's anatomy, physiology and any pathologic conditions. Planar images from a gamma camera are obtained from a single gamma camera position with the use of a collimator, such that the directionality of the photon can be inferred. Parallel collimators provide directionality and the image size is equivalent to the object size. Pinhole collimators are commonly used to image small objects such as the thyroid gland, such that a magnified image can be obtained. A two-dimensional image is produced providing diagnostic information.

A Single Photon Emission Computed Tomography (SPECT) system is also used in nuclear medicine. Once again, the radiopharmaceutical is administered and it distributes within the body. The SPECT system acquired image data using a gamma camera from multiple locations and processes the images such that a three-dimensional data set can be obtained. SPECT images can be overlaid with Computed Tomography (CT) to enhance detection, specifically improving localization within the body.

A Positron Emission Tomography (PET) system is also used in nuclear medicine. The radiopharmaceutical is administered and it distributes throughout the body. The radiopharmaceuticals used in this procedure emit positrons. The positrons travel a short distance in the body and then annihilates with an electron and produces two 511 keV photons, which are emitted approximately 180 degrees apart as shown in FIG. 1.

SUMMARY

Problems with conventional nuclear imaging include: poor spatial resolution due to detector size. The present invention addresses this problem by way of lenses and large distances to provide magnification and spread out photons over large detector arrays.

Another problem is poor spatial resolution due to noncolinearity error wherein the trajectory of the photons is not known when using coincidence detection only. No aim in current PET scan to assess direction of incoming photons, which arise from the location of the annihilation event. Collimation when used in conjunction with collimators and above lens and detector arrays can determine the trajectory of the incoming photon at each detector. Collimation+ precision timing can further increase accuracy of calculated trajectory of the incoming photons at each detector and use time of flight analysis for improved spatial resolution.

Another problem is Noise/image degradation from erroneous Line Of Response (LOR) of a scatter coincidence. In this scenario, coincidence detection would not be used. Collimation would eliminate amount of error from scatter by one half. The unscattered photon would be accurately portrayed. The scattered photon would generate an inaccurate portrayal. Noise is reduced.

Other problems include noise/image degradation from erroneous LOR from a random coincidence. In this case, coincidence detection would not be used. Collimation would eliminate all random coincidences. Noise is reduced.

Further problems include error from site of positron emission. No aim to predict the location of the positron emission. By understanding the trajectory of the photons, the momentum at the time of the annihilation event can be estimated. Thus, the location of the positron emission can also be estimated.

Yet another problem is limitations of PET timing. To address this issue the present invention can alter timing gates to only accept photon pairs if they occur within a narrow timing window with an expected delay. Alternatively, detectors can be moved.

Embodiments of the present invention provide methods and design alternatives for the detection of radionuclides with the use of lenses, mirrors and/or collimators together with a large array of detectors to correct for multiple sources of error including random coincidence and non-collinearity and provides improved spatial resolution and potentially higher efficiency and lower radiation dose.

A conventional PET detector environment 10 is shown in FIG. 1. The PET detectors use coincidence detection to determine the approximate location of the annihilation event by creating a line of response (LOR) from the two detectors. This LOR does not include the annihilation event because the pair of 511 keV photons do not travel away from one another at exactly 180 degrees apart. Thus, even for a true coincidence, the annihilation event does not occur along the line of response and spatial resolution is lost. Also, due to the lack of precision of the clock (and associated duration of the time step during which photons are collected and deemed to be near simultaneous), a region of uncertainty is created along this line, as depicted in FIG. 1. Ultimately, after processing, a three-dimensional data set is obtained. Additional sources of error in PET imaging include scatter coincidence and random coincidence. Scatter coincidence occurs when one of the two 511 keV photons is scattered; this would also alter the line of response from the two detectors, causing a source of error (see PET detector environment 20 in FIG. 2A). Random coincidence involves two annihilation events that occur near simultaneously. The line of response joining the two detectors from separate annihilation events and does not reflect the location of either annihilation event, causing a source of error (see PET detector environment 25 in FIG. 2B). FIG. 1 illustrates positron emission, annihilation event and non-collinearity. Positron emission is a type of radioactive decay, which can be imaged with a PET scan. When the nucleus of an atom contains a high number of protons with respect to neutrons, a type of radioactive decay that can occur is called positron emission. One such example is Fluorine-18, which emits a positron. The black square represents location of positron emission. The positron travels a short distance, called positron range or wandering distance, represented by "d" in the illustration, through tissue and then interacts with an electron and undergoes an annihilation event whereby a pair of photons (e.g., 511 keV photons) are emitted. The black circle represents the location of the annihilation event. Angle θ represents the angle that the two 511 keV photons are emitted from one another, which is close to, but not equal to 180 deg. These photons can be detected with a PET scan and an image can be reconstructed by generating a line of response. The dotted line represents the line of response, which is drawn from the location of the photon hitting detector #1 to the location of the photon hitting detector #2. During the processing, an assumption is made that the photons are emitted at 180 degrees apart. Since this assumption is not accurate, there is an error generated called non-collinearity error; hence, the line of response does not include the location of the annihilation event. This results in loss of spatial resolution from non-collinearity error. There is also a thick black line seen along the line of response illustrated, which represents an uncertainty region along the line of response due to lack of perfect precision in the clock. This uncertainty error is due to the relative distance the annihilation took place from the detectors, which can be referred to as the time of flight. Ultimately, spatial resolution is lost from error of time of flight imprecision (also referred to in this document as time step duration).

FIGS. 2A and 2B provide illustrations of scatter coincidence and random coincidence. A scatter coincidence occurs when one of the photons emitted from an annihilation event impacts some non-absorptive material within the body and its trajectory is deflected (this is represented as the black diamond). In this illustration, the detectors, annihilation event, angle θ, and the pathways of the pair of 511 keV photons are again shows. The pathway of the bottom photon is deviated at the site of a black diamond, which represents the scatter event. Ultimately, the LOR does not accurately represent the location of the site of the positron emission. This results in a line of response generated which can be significantly displaced from that generated when no scattering occurs. Scatter coincidences result in image degradation. A random coincidence is wherein two near simultaneous events have occurred and the two detectors generate a line of response that erroneously joins one of the impact points from two different annihilation events. In this illustration, the detectors are again shown. On the left is an annihilation event, angle $θ_1$, and the pathways of the pair of photons. On the right is a second near simultaneous annihilation event, angle $θ_2$, and the pathways of the pair of photons. There is also a dotted line with a black rectangle illustrated, which represents the line of response, which does not accurately reflect either annihilation event and is a source of image degradation.

The spatial resolution of PET, which some sources say is 6 mm, is considerably worse than that of CT, which some sources say is 0.5 mm. Smaller PET detectors have been developed to attempt to improve spatial resolution, but the error of non-collinearity cannot be corrected, even with a smaller PET detector size.

This presently disclosed method and apparatus for improvement of spatial resolution in molecular and radiological imaging combines nuclear medicine detectors with a system of lenses, collimators, shutters and/or mirrors together with large arrays of detectors to obtain diagnostic nuclear medicine images. Both planar images and three-dimensional data sets can be obtained. Alternatively, these principles can also be applied to plain film x-ray and CT imaging. There are several key limitations in medical imaging, which can be overcome by methods discussed in this patent.

One of the limitations of achieving spatial resolution in nuclear medicine is the detector size. This presently disclosed method and apparatus for improvement of spatial resolution in molecular and radiological imaging uses various design implementations, which utilize the principle of magnification (by lenses) to help overcome the issue of detector size to achieve an improved spatial resolution. These embodiments use the process of magnification to spread out small tightly grouped photons into a larger group and onto an array of detectors, which will provide improved spatial resolution. This process is illustrated in environments 30, 32, 34, 36 and 38 illustrated in FIGS. 3A-3E and described in the flow chart depicted in FIG. 11.

The trajectory of the photons is not known when using coincidence detection. Coincidence detection only relies on near simultaneity of arrival of a pair of photons. The solution to this problem is to use collimators to better focus the photons on to the lens and then on to the detector array. From this, two independent paths of the companion photons can be constructed. The intersection of these paths (within a user specified tolerance) will be the location of the annihilation event. This will reduce the error resulting from non-collinearity. This process is illustrated in environments 40, 42, 44, 46, 47, 48 and 49 illustrated in FIGS. 4A-4F and described in the flow chart depicted in FIG. 12.

Scatter coincidences can cause significant noise in the image. The intersection of the paths calculated in the above step would, in most cases, not meet the tolerances specified and therefore, would be ignored. In the event the two paths are in the same plane, angle would be close to 180 degrees for a non-scatter event (see FIG. 4E) and not close to 180 degrees, (e.g., less than 175 degrees) for a scatter event as shown in FIG. 4F.

In a similar manner to scatter coincidences, random coincidences could be removed through not meeting the criterion of maximum tolerance distance for intersection of the paths of companion, time coincidence, photons as shown in FIG. 4G.

The error induced from the distance error from the positron emission location to the annihilation event can be reduced by bisecting the angle between the two paths and then moving a user specified distance along the bisection line away from the vertices' in the direction of the obtuse angle. This user specified distance can be estimated by factors including the radiotracer used and its positron path length (see environment 50 of FIG. 5).

The error induced by uncertainty region created by the duration of the time step can be corrected by either of two processes: asymmetric positioning of the detector arrays or by non-synchronous time steps between opposing detector arrays. See environment 60 and 65 in FIGS. 6A-6B.

In a particular embodiment of a method for providing improved spatial resolution in molecular and radiological imaging the method includes plotting detectors, lenses and patient in a single coordinate system and plotting known points on detectors based on coincidence detection. The method further includes using laws of refraction and systems of equations to solve for trajectory of photon path. The method further includes plotting the photon paths and plotting a resulting PET data set.

In another particular embodiment of a method for providing improved spatial resolution in molecular and radiological imaging the method includes detecting a pair of photons and utilizing collimation to determine a trajectory of at least one of said pair of photons hitting a detector. The method further includes plotting a path of an incoming photon for a first detector and plotting a path of incoming photon for a second detector. The method further includes assessing an angle between said paths of the photons and a position of intersection of the paths and determining whether said photons are a true coincidence, a random coincidence or a scatter coincidence. Additionally the method includes plotting the true coincidence into a PET data set.

In another particular embodiment of a method for providing improved spatial resolution in molecular and radiological imaging the method includes developing, for all points within a body, a set of voxels and a corresponding set of potential grid matches. The method also includes comparing a set of data with the set of potential grid matches and plotting all matches into a PET data set.

Other embodiments include a computer readable medium having computer readable code thereon for providing improved spatial resolution in molecular and radiological imaging. The computer readable medium includes instructions for plotting detectors, lenses and patient in a single coordinate system and instructions for plotting known points on detectors based on coincidence detection. The computer readable medium further includes instructions for using laws of refraction and systems of equations to solve for trajectory of photon path. The computer readable medium further includes instructions for plotting the photon paths and instructions for plotting a resulting PET data set.

In another particular embodiment, the compute readable medium for providing improved spatial resolution in molecular and radiological imaging includes instructions for detecting a pair of photons and instructions for utilizing collimation to determine a trajectory of at least one of said pair of photons hitting a detector. The computer readable medium further includes instructions for plotting a path of an incoming photon for a first detector and instructions for plotting a path of incoming photon for a second detector. The computer readable medium further includes instructions for assessing an angle between said paths of the photons and a position of intersection of the paths and instructions for determining whether the photons are a true coincidence, a random coincidence or a scatter coincidence. Additionally the computer readable medium includes instructions for plotting the true coincidence into a PET data set.

In another particular embodiment, the computer readable medium for providing improved spatial resolution in molecular and radiological imaging the computer readable medium includes instructions for developing, for all points within a body, a set of voxels and a corresponding set of potential grid matches. The computer readable medium also includes instructions for comparing a set of data with the set of potential grid matches and plotting all matches into a PET data set.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides improved spatial resolution in molecular and radiological imaging as explained herein that when performed (e.g. when executing) on the processor, operates as explained herein within the computerized device to perform all of the method embodiments and operations explained herein as embodiments of the invention. Thus any computerized device that performs or is programmed to perform the processing explained herein is an embodiment of the invention.

Other arrangements of embodiments of the invention that are disclosed herein include software programs to perform the method embodiment steps and operations summarized above and disclosed in detail below. More particularly, a computer program product is one embodiment that has a computer-readable medium including computer program logic encoded thereon that when performed in a computerized device provides associated operations providing improved spatial resolution in molecular and radiological imaging as explained herein. The computer program logic, when executed on at least one processor with a computing system, causes the processor to perform the operations (e.g., the methods) indicated herein as embodiments of the invention. Such arrangements of the invention are typically provided as software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. The drawings are not necessarily to scale, emphasis instead being placed upon illustrating the principles of the invention.

FIG. 2A is an illustration of scatter coincidence and FIG. 2B is an illustration of random coincidence.

DETAILED DESCRIPTION

Figure 1:
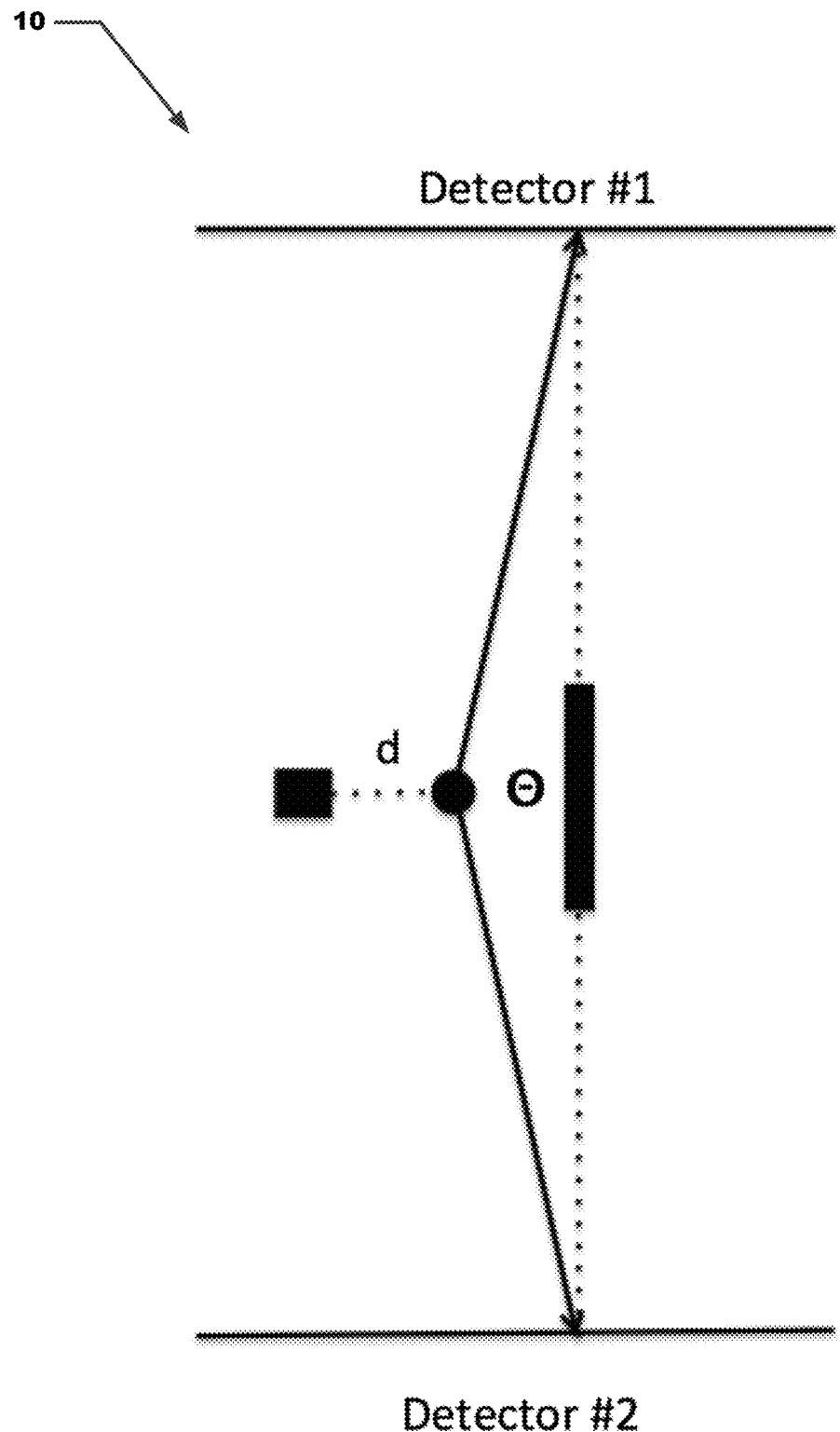
FIG. 1 is an illustration of positron emission, annihilation event, non-collinearity and time of flight error.
Figure 3A:
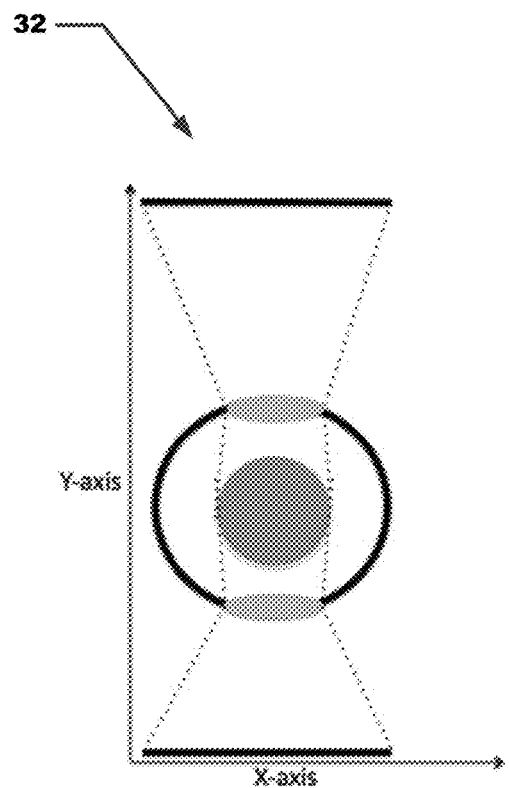
FIG. 3A-3E are illustrations of design implementations which provide improved spatial resolution.
Figure 3B:
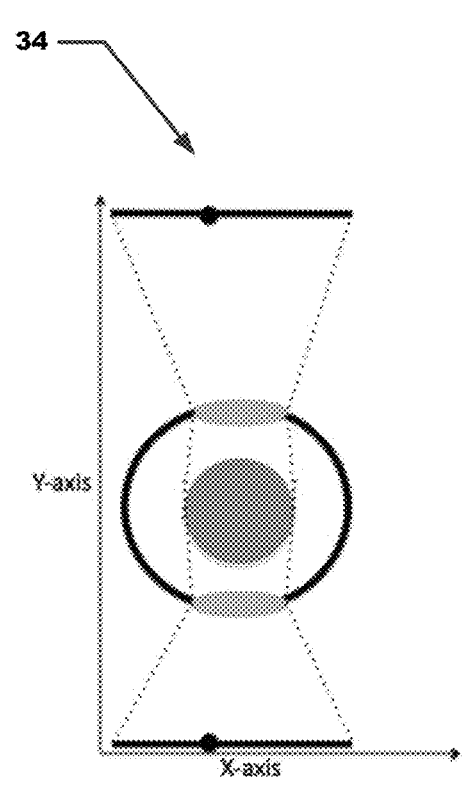
Figure 3C:
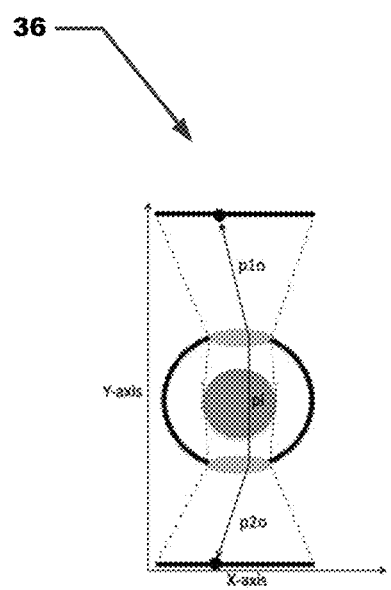
Figure 3D:
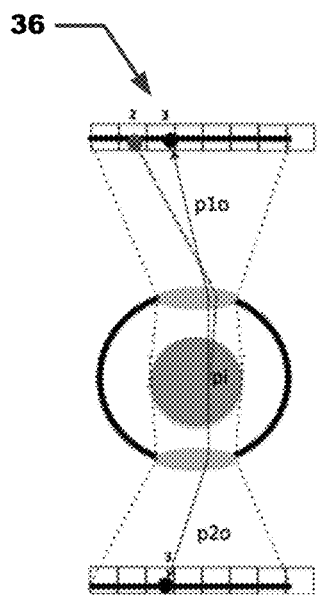
Figure 3E:
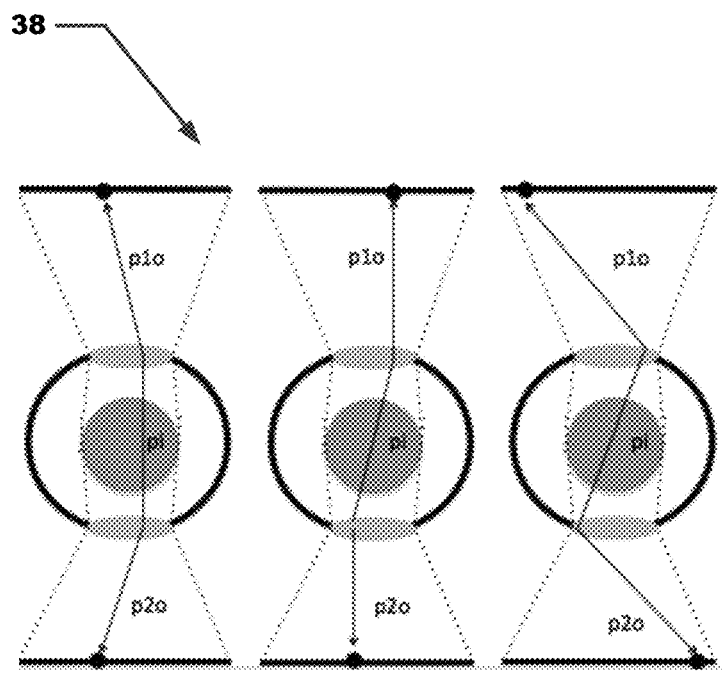
Figure 4A:
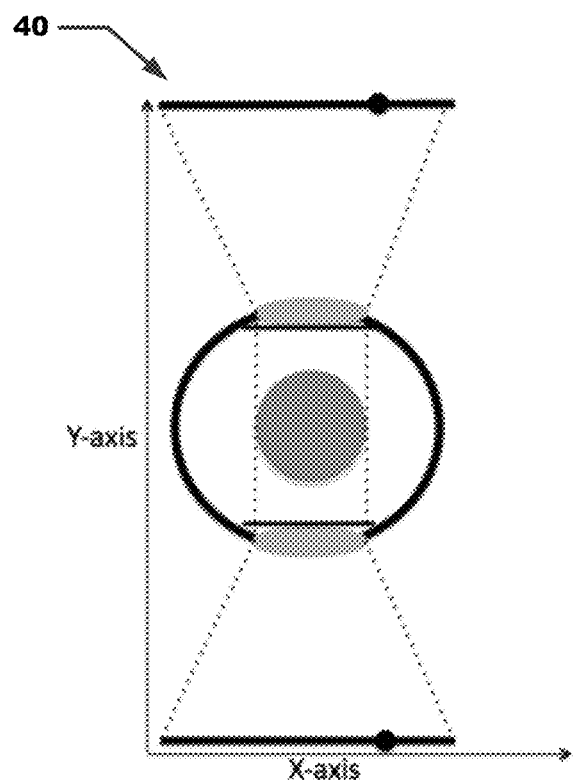
FIGS. 4A-4G are an illustration of the design implementation with the use of collimation.
Figure 4B:
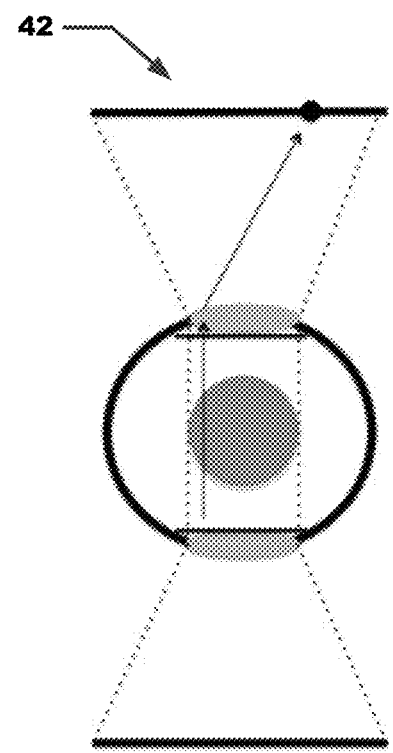
Figure 4C:
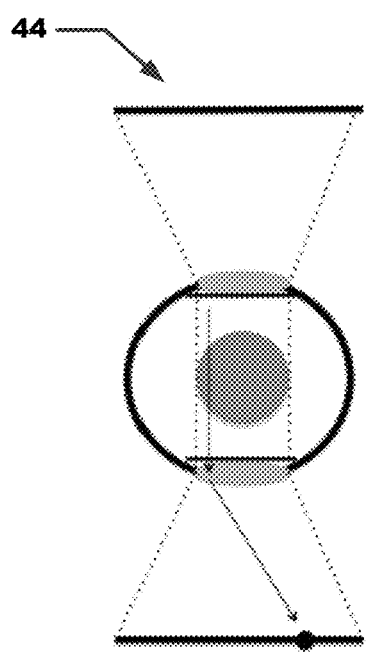
Figure 4D:
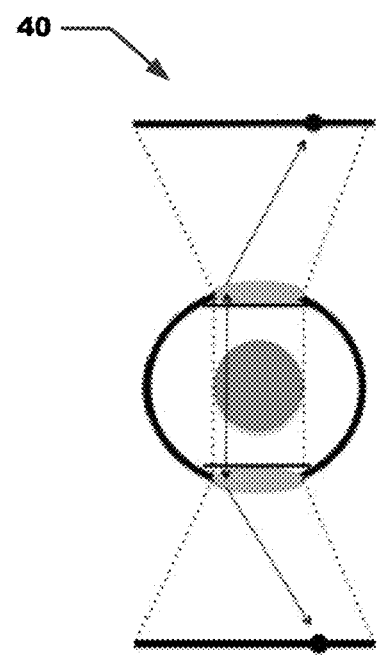
Figure 4E:
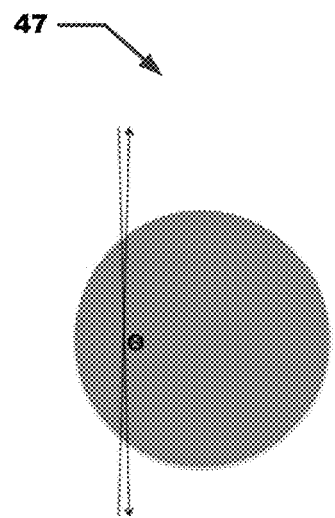
Figure 4F:
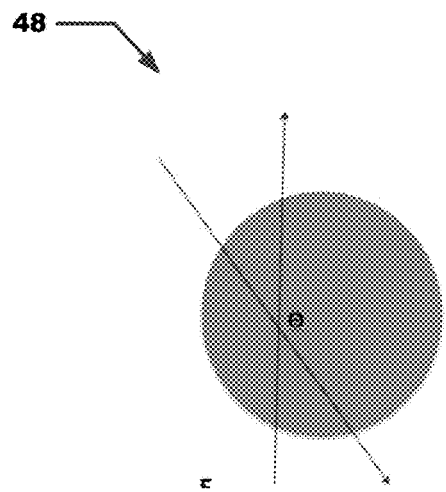
Figure 4G:
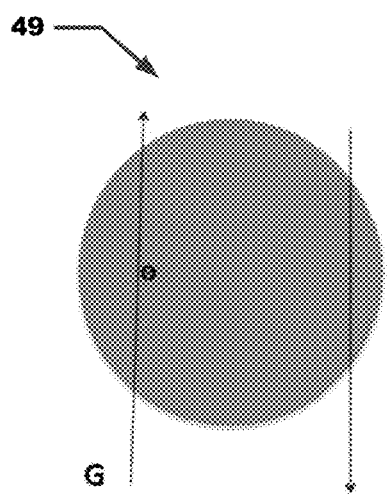
Figure 5:
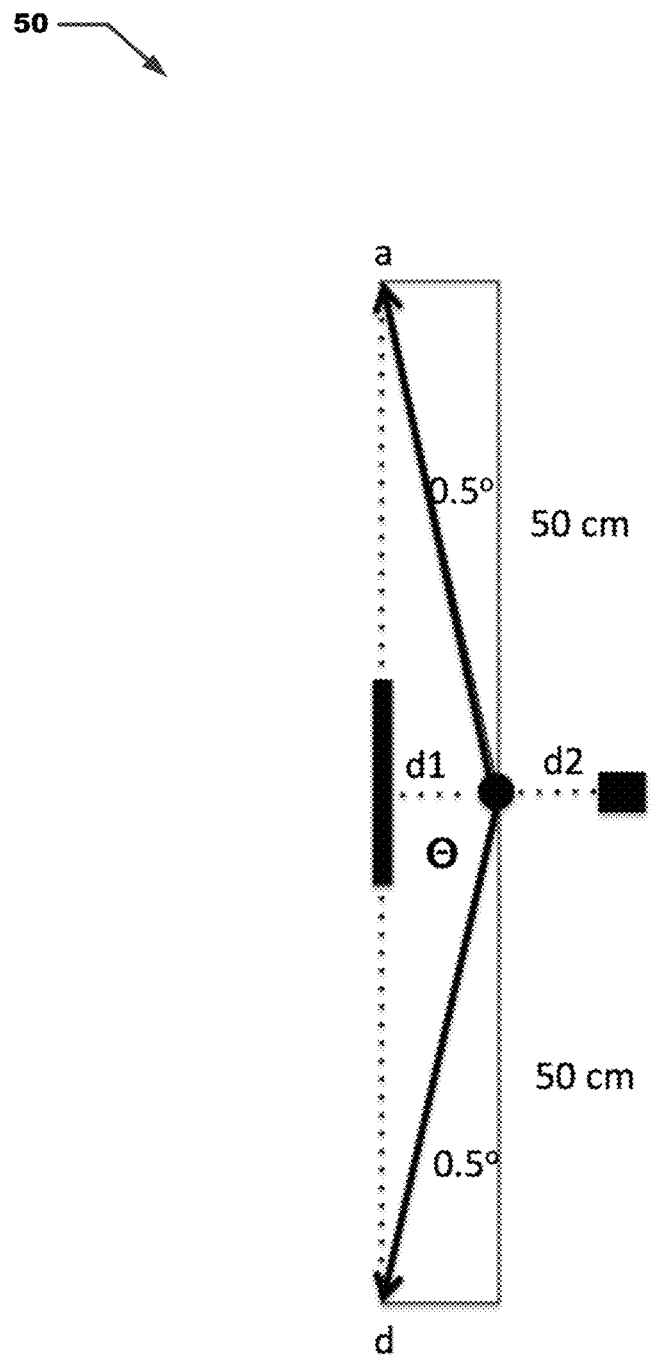
FIG. 5 is an illustration of calculation of improved spatial resolution due to correction of non-collinearity error and error from location of positron emission.

The embodiments set forth below represent the necessary information to enable those skilled in the art to practice the invention and illustrate the best mode of practicing embodiments of the invention. Upon reading the following description in light of the accompanying figures, those skilled in the art will understand the concepts of the invention and recognize applications of these concepts not particularly addressed herein. It should be understood that these concepts and applications fall within the scope of the disclosure and the accompanying claims.

The preferred embodiment of the invention will now be described with reference to the accompanying drawings. The invention may, however, be embodied in many different forms and should not be construed as limited to the embodiment set forth herein; rather, this embodiment is provided so that this disclosure will be thorough and complete, and will fully convey the scope of the invention to those skilled in the art. The terminology used in the detailed description of the particular embodiment illustrated in the accompanying drawings is not intended to be limiting of the invention. In the drawings, like numbers refer to like elements.

Finally, this presently disclosed method and apparatus for improvement of spatial resolution in molecular and radiological imaging provides a scheme to record the data using a 3 dimension coordinate system.

This presently disclosed method and apparatus for improvement of spatial resolution in molecular and radiological imaging provides a method and design alternatives for the detection of radionuclides with the use of lenses, mirrors and/or collimators together with a large array of detectors to correct for these multiple sources of error.

A further element of this presently disclosed method and apparatus for improvement of spatial resolution in molecular and radiological imaging is to combine multiple imaging modalities into a single machine. The motivation for this is that an inhibitor for many hospitals that precludes them from investing in either SPECT or PET is the cost of the equipment relative to the case load requiring these services. In many cases the combined case load from SPECT and PET would justify acquiring a combined imaging machine which used a high fraction of the same components. The innovation covered here is that the imaging machine would have two cylinders arranged such that the gurney would be positioned under the appropriate set of detector arrays for imaging task at hand. Key components discussed in the previous paragraph would be required for both detector arrays including crystals for detection of both single photon radioactive decay and dual photon positron decay. For example: the arrays of lenses and collimators would be dual use; the electronics would be dual use; the physical structure housing the full set of components would be dual use as would the mechanical elements for movement of the placement of the patient. For many hospitals, only a single room would have to be set aside for this purpose, reducing total set-up costs.

The final element covered under this presently disclosed method and apparatus for improvement of spatial resolution in molecular and radiological imaging is to combine a CT scanner with the above combination of detector arrays including crystals for detection of both single photon radioactive decay and dual photon positron decay. The motivation for this is complementarity of the technologies i.e., CT depicts relative densities within the body, whereas nuclear imaging responds to chemical uptake. The advantages obtained by this innovation are: capability to combine CT with the high resolution single photon detection; capability to combine CT with high resolution dual photon detection. A further advantage is that the set of images obtained would be taken under the same status/condition of the patient.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

Example alternative apparatus implementations are described in this section. It should be noted there is a very large number of possible implementations due to the differing types of components and multiplicity of designs within any particular type of component. This presently disclosed method and apparatus for improvement of spatial resolution in molecular and radiological imaging is intended to cover each of this large number of possible implementations. Alternative apparatus implementations are applicable to the both high resolution single photon detection and high resolution dual photon detection. These nuclear medicine imaging modalities can also be combined with other radiology imaging modalities including MRI and CT. Within these types of medical imaging modalities there could be various types of components including the following.

Collimator(s) of multiple types, such as parallel narrowly spaced cylinders, diverging cylinders, and converging cylinders. Cylinders may be of varying diameters and lengths. Pinhole collimator(s) which may provide directional information and performs magnification or minification depending on the relationship between the object being imaged; pinhole collimators may have small or large apertures and narrow or wider field of view (FOV). Collimators can be changed in order to match the radioisotope administered to the patient in order to optimize the efficiency of collection effort.

Lenses of various materials and properties such as diameters and curvature. Arrays of micro lenses, and used in in conjunction with other lenses.

Mirror(s) including single or multiple mirrors associated with collimator(s) or lens to direct photons onto specific detectors. Fast steering mirrors to sequentially direct photons to different detectors. Planar or curved mirrors.

Shutter(s) associated with lens or collimator(s) to be opened and shut according to a planned collection of images.

Detectors including current detectors, such as 6 mm. A variety of crystals used, such as sodium iodide as is currently used in current SPECT scanners or BGO or LSO crystals as is currently used in current PET scanners. An array of detectors—arbitrary size to generate desired level of resolution. Advanced detectors with smaller size and/or greater sensitivity. Detector arrays can be changed in order to match the radioisotope administered to the patient in order to optimize the efficiency of collection effort.

Image and signal processing such as amplification of the light per unit area on images obtained by combining the output of detector array(s).

Variations in detector array positioning including truncation of the length of the uncertainty region (induced by limitations of time step duration) through the use complimentary images (e.g., orthogonal). Physical re-positioning of one set of detector arrays prior to the imaging process such that there is an asymmetric distance between arrays focused on a specific region of interest to reduce the length of the uncertainty region induced by limitations of the time step duration.

Example combinations of components in differing arrangements are shown in FIGS. 8A-8E.

Environmental—depending on local conditions, the above components may be hermetically sealed.

A variety of scalable media including electronics, data processor, and recording medium to consistent with data loads will be used in conjunction with the apparatus. Standard reconstruction methods may be used.

A systems approach should be taken whereby top level trades would include, but are not limited to: specific purpose of the device (e.g., scan for possible tumor); required level of resolution associated with the purpose of the device (e.g., be consistent with CT at 0.5 mm); patient considerations (e.g., maximum time allowed within the imaging enclosure, dosage level constraints); budgetary issues (e.g., procurement costs, operational costs); and facility considerations (e.g., size of imaging room, power requirements).

Figures 9A, 9B:
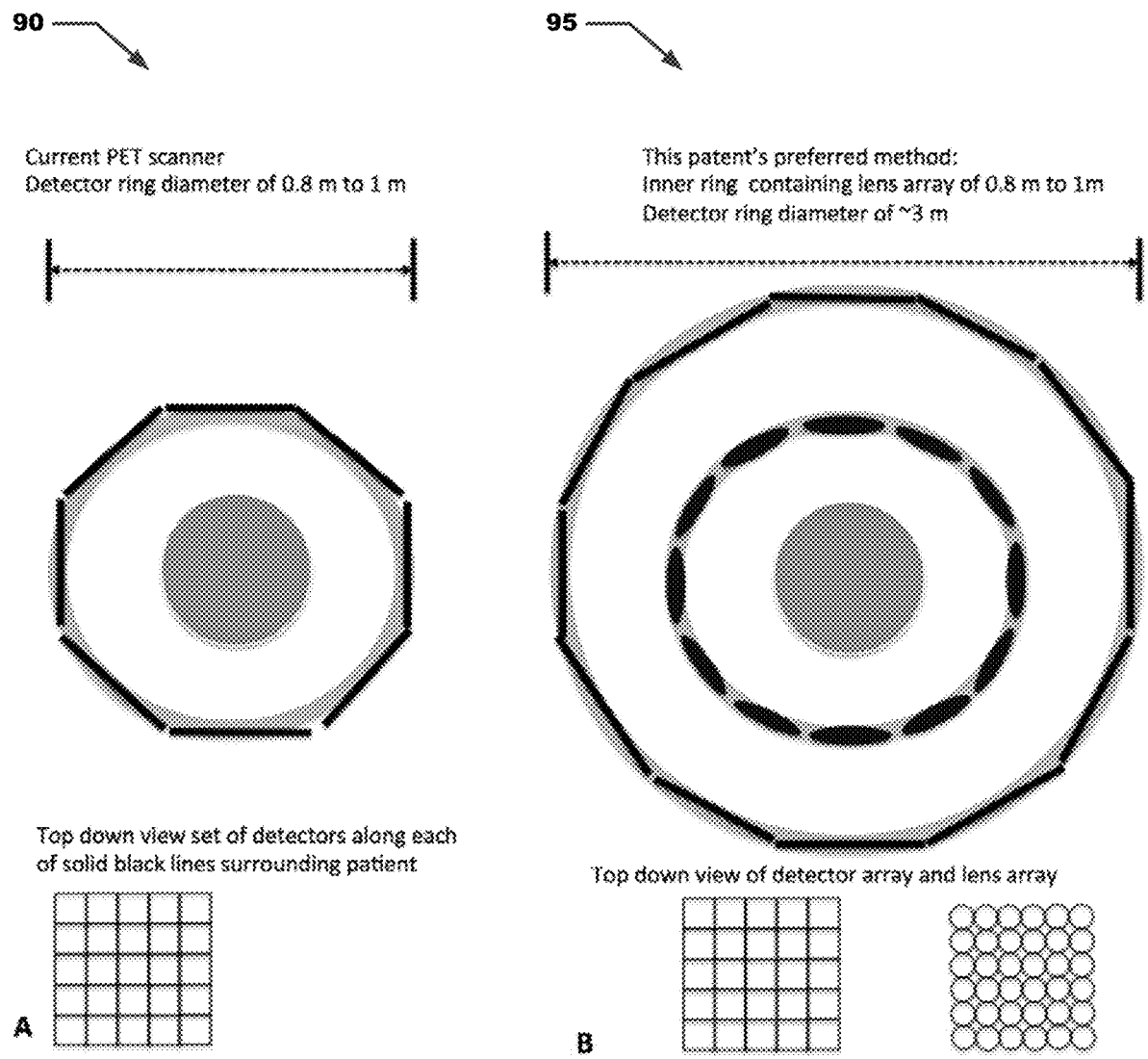
FIGS. 9A-9B are illustrations of an example nuclear imaging apparatus.

One alternative implementation includes the following. At the present time, the patient is surrounded by a ring of detectors. Implementation configuration includes placing a lens at current location of detector. Placing a detector array some distance further. For example, if the diameter of the inner surface of the current set of detectors is 1 meter, and the circumference is 3.14159 meters then with 6 mm detectors, there would be approximately 524 detectors in the current arrangement. If the detectors were placed an additional 1 meter from the lens, this would require an additional 1046 detectors (FIGS. 9A and 9B). A further reduction if the error can be achieved by the following. An assumption for this process is that the lenses are small—the diameter of which is a size on the order of the current detector diagonal. Draw a straight line (line #1) between the center of the lenses in front of the detector arrays where photons near simultaneously were received. Calculate the uncertainty region along this line (based on lack of absolute precision of clock timing the arrival of photons arriving at the detector array) and calculate the location of the midpoint of this uncertainty region. (Note: if some portion of this uncertainty region has been truncated per other portions of the patent, calculate the midpoint of the non-truncated uncertainty region.) Arbitrarily pick any one of the 2 detector arrays (call it array #1) where the photons were received. Project that line (step #1) through the lens (lens #2) associated with array #2 and see which detector a photon originating along that line would land on. Calculate the angle between the line (step #1) and an additional line (line #2) drawn between the midpoint of uncertainty region (step #2) and where on the lens a photon would have had to have landed on lens #2 in order for it to arrive at the actual detector the photon arrived at. Cut this angle in half and, in the same plane as lines #1 & #2, project a new line (line #3) toward lens #2 and determine new intersection point on lens #2. Label this new point—Point B. Create a new line (line #4) from Point B to the center point of lens #1. Calculate the angle between line #4 and a new line (line #5) drawn between the midpoint of uncertainty region (step #2) and where on the lens a photon would have had to have landed on lens #1 in order for it to arrive at the actual detector the photon arrived at on detector array #1. Cut this angle (Step #7) in half and, in the same plane as lines #4 & #5 and project a new line (line #6 toward lens #1 and determine new intersection point on lens #1. Label this new point—Point A.

Draw a new line from Point A to Point B. Recalculate the uncertainty region and place it along Line A-B. The benefits of the above are, if one assumes the current co-linearity errors are on the order of 2 mm and the uncertainty bar is 5 mm then, using the dimensions in the above example, then: the added detectors reduce the error by a factor of three (using the above dimensional changes, above). This is an example implementation of magnification. The above process will further reduce the residual error by approximately 50%.

An example of a frequent condition is one wherein there is knowledge about the approximate location of an unusual mass in the body, but the exact size, shape, etc., are not fully understood. Currently, a large fraction of the lines of response portrayed on the image are extraneous and could be considered 'noise'. This high level of noise inhibits a crisp picture of the unusual mass and renders accurate diagnosis difficult.

A further example of one embodiment of the present invention is to use collimators in conjunction with the lenses and detector arrays described above. Place a set of collimators between the patient and the lenses. These collimators could either be parallel or at small angles such that they converge at some pre-calculated distance and volume subtended. It is envisioned that the particular set of collimators would be exchangeable within the apparatus and that there would be a variety of these collimators of different designs which would be available and a particular one would be selected by medical personnel. Adjust the height and position of the patient within the apparatus such that the volume of interest (e.g., unusual mass) will be at the optimal location for retrieving photons from this volume. After the proscribed time to collect the imagery, apply light amplification processing to the imagery. Note that this is possible due to the significant reduction in extraneous noise, based on only photons generated from the subtended volume observed by the collimators would be present. Note also that light amplification processing is of no value under the current conditions in that this processing would only make the noise brighter/more intense.

The benefits of this configuration include the resulting image has significantly lower noise than is the case with the current technology. As a result the surface of the tumor is more clearly defined, thus permitting a higher degree of confidence in the diagnosis. It is possible to use lower dosages of radioactive materials through application of light amplification. The lower dosage in turn reduces the risk to the patient for cancers/tumors resulting from higher levels of radiation.

Another configuration could be employed where the location of the mass is known and additional detail regarding the shape, size, etc. is needed. This configuration would include the following. A series of arrays, each of which have collimators that converge on a predetermined volume at a specified distance for the forward edge of the collimators. Lenses associated with each of the collimators, as previously described. Filters that would permit collection from only specified fields of view (FOV) (e.g., a truncated frustum shaped FOV with the truncated portion at the lens and the base of the frustum oriented toward the detector array). A detector array as previously described. Software to apply light amplification, as previously described. Further software which would truncate the length of the uncertainty lines could also be invoked. This configuration could be used in the following manner. An initial collection could be taken from orthogonal directions (e.g., from the cardinal directions: 0°, 90°, 180°, 270°). The filter element could be rotated by a specified angle (e.g., 30°) and a different set of images collected. The filter element could be further rotated by a specified angle (e.g., 30°) and an additional set of images collected, this rotation of the filter element would continue through the observation angles required by the physician.

The benefits of this configuration are as follows. A very precise 3D representation of the tumor (or other object) could be obtained. This would enable a more accurate diagnosis of the patient's condition. Regions of interest which are currently fuzzy due to regions of uncertainty along lines of coincidence will be rendered sharp.

In another embodiment, y analyzing the path of each photon and intersection of this path with the path of time related path other photon, rather than creating a line of response, there is no loss of spatial resolution due to non-collinearity. Note that the individual trajectories of the photon paths are plotted; not the lines of response. It should be noted that the accuracy of the path (or the uncertainty volume surrounding the estimate of the path trajectory) could be significantly improved with the inclusion of other components addressed in this patent. During the processing of the data from the PET scan, the individual photon paths will be processed in the analysis, not the lines of response. Specifically, no spatial resolution will be lost due to non-collinearity.

Example processes to reduce uncertainty region. In a first particular embodiment a method to reduce uncertainty region due to clock imprecision. During each clock cycle, conceptually there are bands of distance from the detector: the farthest distance band would connote an instance when the event occurred just as the cycle was beginning and the photon arrived just as the cycle was ending; conversely, the shortest band would occur in an instance when the photon event occurred late in the clock cycle and the photon arrived just prior to the cycle ending. The overlap of these distance bands of paired detectors creates the uncertainty region. Next suppose that the distance of the detectors from the patient was variable. By varying the distance of each of the detector of the paired detectors (or detector arrays) only a small volume would be overlapped. Events would only be recorded for this small volume which occurred when the event took place at the beginning of the clock cycle and a photon arrived at the more distant detector array and the companion photons arrived just before the clock cycle ended at the nearer array. By varying the distance in an asymmetric manner, only a specific volume of interest would receive events. Note that the volume above could be arbitrarily small. And, by moving the paired detectors appropriately over time, a region of interest could be investigated. This would enable pinpointing anomalies.

A second process is used to reduce uncertainty region due to clock imprecision. Consider the above process of moving paired detectors (detector arrays). There is another way to achieve a small region of overlap for paired detectors (detector arrays): an event occurred near the end of clock cycle N was recorded by one of the paired detectors (detector arrays) and at the beginning of the clock cycle N+1 at the other paired detector (detector arrays). The same sizing of the volume of interest and movement of this volume could be achieved by changing the start time of the clock cycle of one of the paired detectors (detector arrays). By so doing, anomalies could be pinpointed. As an example wherein both Process #1 and #2: would be exceptionally valuable would be in the case evaluating small, but extremely important structures such as the pituitary gland. Pinpointing the specific region where the pathology is located would be exceptionally helpful for subsequent surgery.

An alternative embodiment is the combination of pinhole collimator(s), mirror(s), lens(es), shutter(s), detector array(s) with the use of an X-ray tube as is used in radiography, fluoroscopy and CT. The principles of magnification and redirecting the photons onto a larger detector would apply in a similar fashion as in the previously discussed examples. There are multiple clinical applications where a higher spatial resolution would be beneficial. First, an example in the field of radiography is provided. In the field of mammography, the detection of microcalcifications requires high spatial resolution. This advance with improved spatial resolution would provide better visualization of the microcalcifications and the possibility for improved detection of breast cancer. Another example is in the field of fluoroscopy and interventional procedures. When the neurointerventional radiologist is visualizing a small aneurysm, it is important to characterize the morphology of the aneurysm as best as possible. The higher spatial resolution will help to better characterize the aneurysm. Another example is in the field of CT angiography of the brain. High spatial resolution may help to classify disease such as vasculitis, which typically involves the small arteries of the brain. Improved spatial resolution may have important clinical applications.

Another alternative is an expansion of alternative #1 with the following modifications: provisions would be made for inclusion of alternative sets of collimators to be inserted at the discretion of medical personnel; both the set of lenses and collimators (when in use) are moveable. There would be two different types of detector arrays: the first set consisting of crystals for detection of single photon radioactive decay and the second set of crystals for detection of dual photon positron decay. Both the lenses and collimators would be positioned between the patient and either set of detector arrays. The gurney with the patient would be positioned under the appropriate set of detector arrays called for by the procedure.

A next alternative would build on the prior alternative described above. A CT scanner would be added. Under this configuration, the normal sequence of imaging would be: place the patient in the correct position and perform a CT scan; next move the patient to a position within the volume scanned by either the set of crystals for detection of single photon radioactive decay or the set of crystals for detection of dual photon positron decay. Finally, ensure correct placement of lenses and collimator (if used) between the patient and the detector arrays. (Recall FIG. 10).

A method and apparatus is described which provides a system for detection of radionuclides or radiopharmaceuticals within the body. This system would nominally be used by nuclear medicine physicians and radiologists for the purposes of medical diagnosis. Example radiopharmaceuticals in which this patent would be useful include detection of technetium-99m agents as well as Fluorine-18 (F-18) agents, such as FDG.

The invention comprises a system of collimator(s), lens (s), mirror(s) and shutter(s) to detect radioactive elements and display them onto a detector array. Advantages include higher spatial resolution by the use of a larger detector array, lower cost by using an apparatus such as a single large detector and lower dose, lower dose by a higher efficiency.

Figure 11:
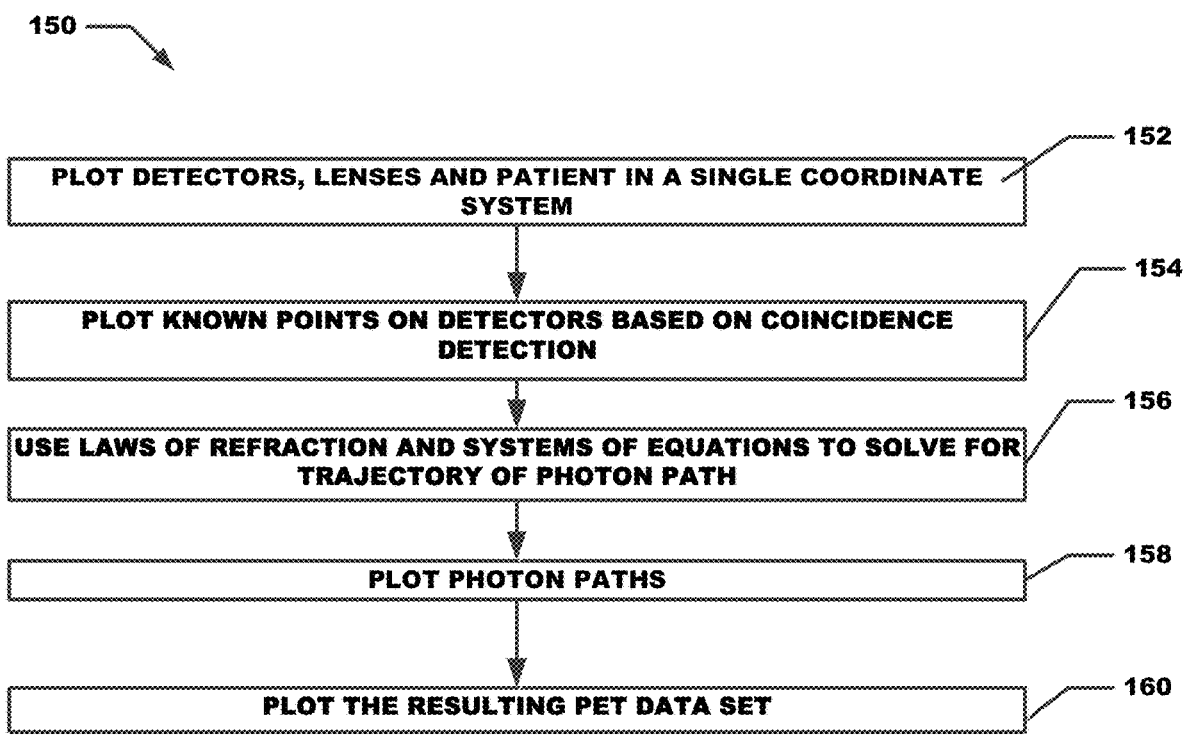
FIG. 11 is a flow diagram of a first embodiment of a method for providing improved spatial resolution of molecular and radiological imaging in accordance with embodiments of the present invention.

Illustration of overview of design implementation discussed in FIGS. 4A-4G and the flow diagram of FIG. 11 without use of collimator (A) Step 1: Overview of the device plotted onto a coordinate system. Detector array #1 (thick black line at top). Lens #1 (light gray oval at top). Axial cross section of patient (dark gray circle) within the cylindrical device (black circle). Dotted lines represent photons emitted from patient, which can be detected; should photons be emitted outside of these margins, they would be attenuated by the cylindrical device in this particular embodiment. Detector array #2 (thick black line at bottom). Lens #2 (light gray oval). (B) Step 2: Plot known points on detectors based on coincidence detection. Each photon striking the detector array is marked as a black circle. (C) Step 3: Use system of equations to solve for the trajectory of the photon path. Assume that pair of 511 keV photons travel away from one another at 180 degrees apart. The laws of refraction govern the correlation between photon path inside the cylindrical device to photon through the lens to the path outside of the cylindrical path. Solve system of equations with 2 known elements (i.e., points (x, y) on detector elements on detector arrays #1 and #2, respectively) and 2 unknowns (i.e., m and b) from slope equation of y(x)=mx+b. Similar mathematical processes can be performed with x, y, z coordinate system. Plot the trajectories of the 511 keV pair of photons. Three slopes are present in this diagram including: p1o (detector element on detector array #1) to lens #1 outside the cylindrical device; pi (lens #1 to lens #2); p2o (detector element on detector array #2) to lens #2 outside the cylindrical device. Embodiment as described will not correct for non-collinearity due to the assumption that the photons are emitted at 180 degrees apart. In order to correct for non-collinearity error, the entering trajectory of the photon at the detector must be known for this to occur; see collimation discussion later in this patent. Standard time-of-flight analysis used in order to better localize the annihilation event. (D) Step 3 continued: Regarding the assumption that the two photons produced were ejected at exactly 180 degrees from one another at the center of the patient, then they would impact detector elements #3 at both the top and bottom detector arrays. The displacement of pi from the center line thru the lenses causes a shift of angle which can be computed and is based on the shape of the lens. However, since the photons are not ejected at exactly 180 degrees, this shift in ejection angle will cause one of the photons (dotted line) to strike the top detector element #2, in this illustration. (E) Step 4: Ultimately multiple various photon paths are calculated. These are plotted in the PET data set.

Overview of a design implementation discussed in the patent including a method and apparatus (e.g., system of lenses, parallel collimators and large detector arrays), which will provide magnification and higher spatial resolution using coincidence detection and collimators.

Illustration of the design implementation discussed in FIG. 6 with the use of collimation. (A) Step 1: Overview of the device plotted onto a coordinate system. Note that this image includes an additional black line adjacent to the lenses, which represents the collimator(s). Plot the coincidence detection to determine a pair of 511 keV photons and use collimation to determine the trajectory of at least one of the photons hitting the detector. Note that the trajectory of the other 511 keV photon in the pair can be derived. Note that the collimator may be placed in conjunction with the lens apparatus or with the detector, multiple types may be used (parallel collimator just inside the lenses are illustrated). (B) Step 2: Plot path of incoming photon for detector array #1. (C) Step 3: Plot path of incoming photon for detector array #2. (D) Step 4: Plot the course of photon #1 and photon #2. Assess the angle between the paths of the incoming photons and the position of intersection of the paths. Determine whether the pair of 511 keV photons is a true coincidence, random coincidence or scatter coincidence. This angle can also be used to help determine the location of the positron emission. (E) Step 4: Assess the angle between the paths of the incoming photons and the position of intersection of the paths. Analyze the angle of intersection of the photon plots. This illustrates a zoomed image with the gray circle represents the cross-section of the body. Each arrow demonstrates the trajectory of the photon. The purpose of this step is to measure the angle between the photon paths, $\phi$. Thresholds, can be set to select for true coincidences. For example, if $\phi$ is between 179 and 181 degrees, the event can be categorized as a true coincidence. A true coincidence is expected to have an angle of ~179.5 degrees for F-18 and is shown. (F) Step 4: If the angle measured is not expected to correlate to that of a true coincidence, then the coincidence event can be rejected and not plotted into the final PET data set. For example, the angle shown is ~140 degrees. This would be rejected as it would not be characterized as a true coincidence and could represent a scatter coincidence or a random coincidence. (G) Step 4: In addition to measuring the angle of intersection, the analysis would have an inclusion criterion that the annihilation event must occur within the body to be plotted. This shows an angle of 179.5 degrees; however, it does not intersect within the body. Finally, other skew lines would also be rejected. After the true coincidences have been accepted and the remainder of coincidences rejected, processing can occur via methods including filtered back projection.

Illustration of calculation of improved spatial resolution due to correction of non-collinearity error and error from location of positron emission. From analysis previously described in this patent (e.g., using system of lenses and collimators), the direction of the path of the photon is obtained. Precise timing between detector array #1 and detector array #2 performed such that a match of 511 keV photons is made. Direction known and match known; therefore, calculate location of annihilation event, shown as circle. Geometric analysis reveals the calculation of angle $\phi$. Distance d and location of the positron emission, black square, can be estimated by correlating the energy of the positron with the previously described geometric analysis. Assume distance from point 'a' to point 'd' on the detector is 100 cm and $\phi$ of 179 degrees, geometric analysis of a right triangle reveals d1=1.7 mm, which represents loss of spatial resolution due to non-collinearity. By analyzing the direction (or path) of each photon, rather than creating a line of response, the non-collinearity error is corrected. In addition, with the knowledge of conservation of momentum, the position of the positron emission, d2 can be estimated.

Figure 6A:
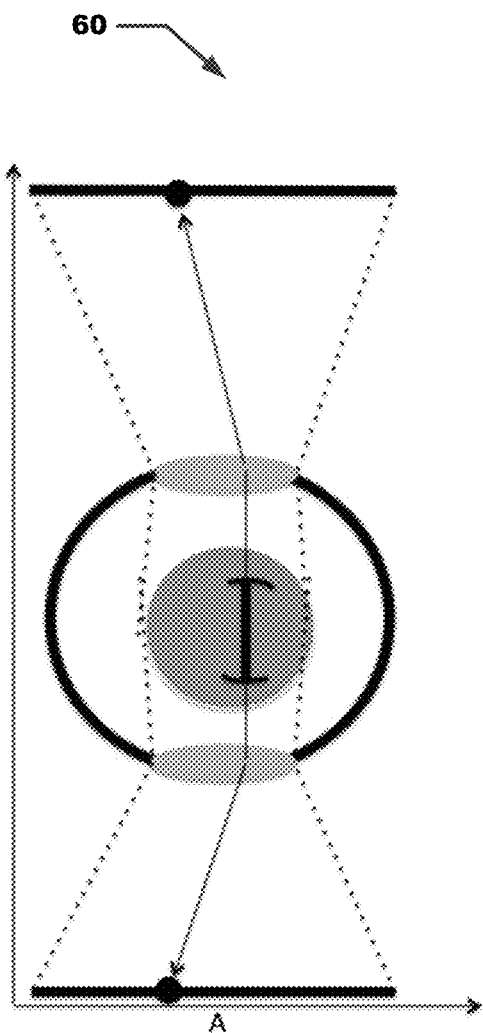
FIGS. 6A and 6B are illustrations both symmetrical positioning of detector arrays and asymmetrical positioning of detector arrays.
Figure 6B:
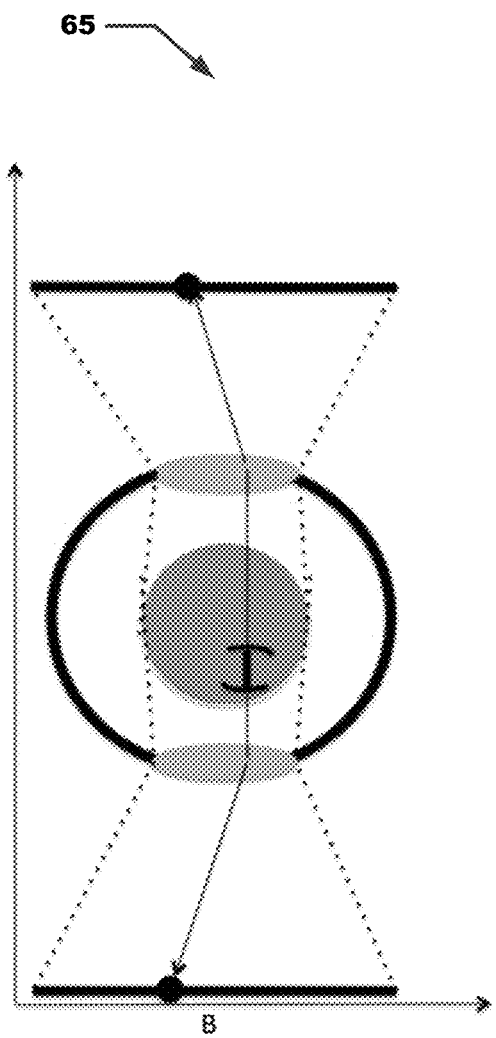

FIG. 6A illustrates a symmetrical distance between detector arrays; the uncertainty in the dark solid portion of the solid line joining the two lenses; and arcs on either end of the solid portion which represent bounds on this region based on the duration of the time step. FIG. 6B illustrates an asymmetrical placement of the detector arrays and consequent reduction in the uncertainty region. Note that some of the events that would have been recorded with the Figure (A) arrangement will be missed in that they would have occurred in a different coincidence time steps at the detector arrays. The advantage of this asymmetry is a reduced size of the region of uncertainty. An underlying assumption in the figure is that the time steps are synchronous. A shift in time (t0=0 to t0=t0+) for one of the detector arrays would result in asynchronous collection of events and depending on the duration of the overlapping time period between detector arrays when a single coincidence event could have a similar reduction in the region of uncertainty.

Figure 7A:
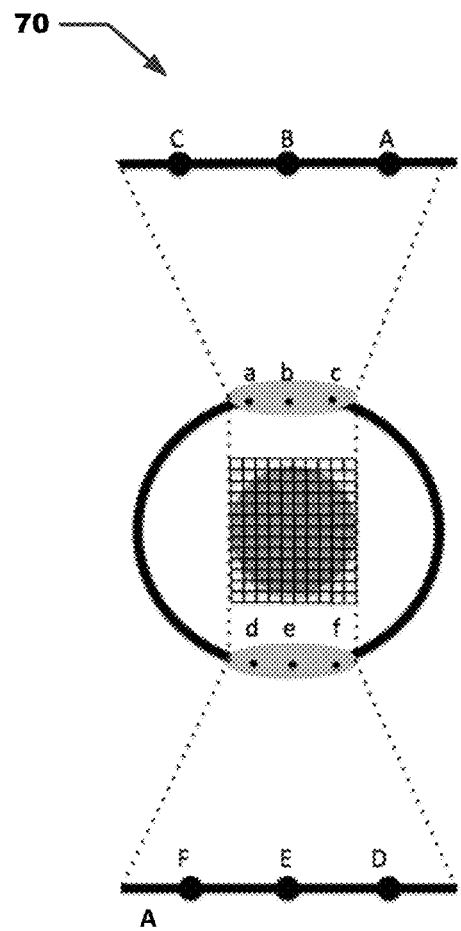
FIG. 7A-7B are an illustration the three dimension coordinate system used to record images.
Figure 7B:
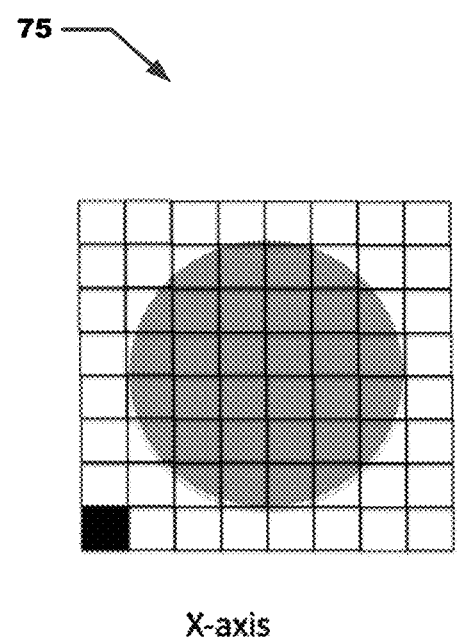

Illustration demonstrating method for processing of data as described in FIGS. 7A-7B. In FIG. 7A For all points within the body, develop a set of voxels (3D matrix) and a corresponding set of potential detector matches. Perform correlation between the coordinate location of the annihilation events, separation angle of the annihilation events, time of flight analysis and the detectors that would be activated. FIG. 7B shows this process can be started at coordinate system x, y, z of (0, 0, 0) and would be repeated for all points in the imaging volume.

Figure 8A:
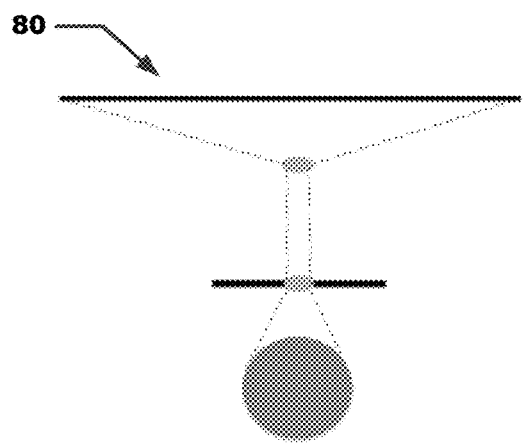
FIGS. 8A-8F are illustrations of multiple example configurations of components covered in this patent.
Figure 8B:
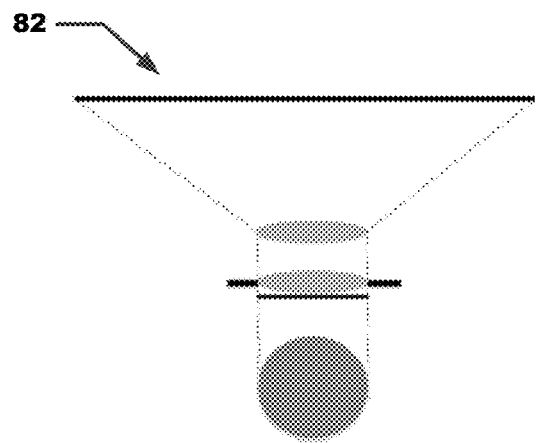
Figure 8C:
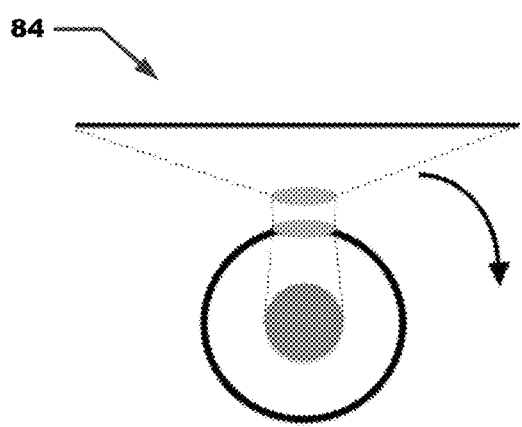
Figure 8D:
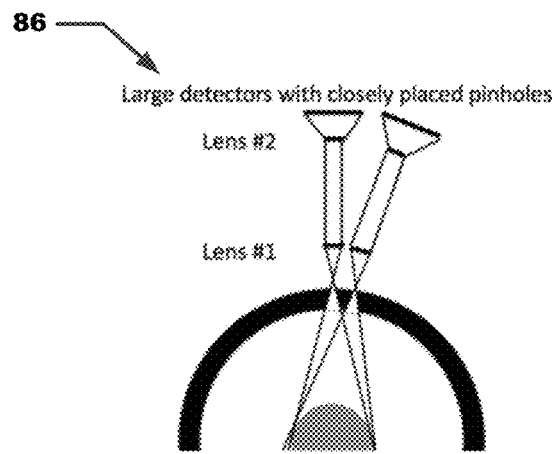
Figure 8E:
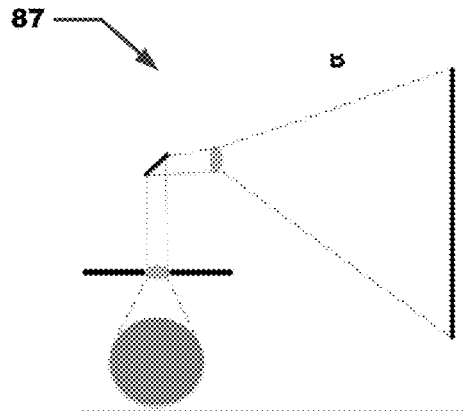
Figure 8F:
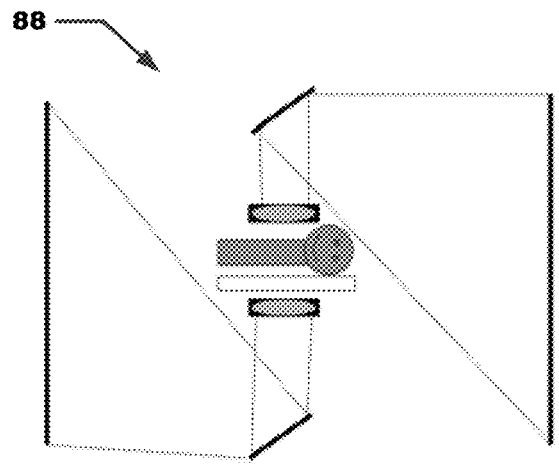

Alternative design implementations. Referring to FIG. 8A the large round gray circle represents the patient. The dashed lines represent the photons emitted from the body, which travel through the lens (gray oval with black line) to the second lens and then to the large detector array (long black line). In FIG. 8B the large round gray circle represents the patient. The dashed lines represent the photons emitted from the body, which travel through the collimator-lens apparatus (gray oval with black lines) to the second lens and then to the large detector array (long black line). In FIG. 8C the large round gray circle represents the patient. The large black circle represents the cylindrical device. The dashed lines represent the photons emitted from the body, which travel through the first lens (bottom gray oval) to the second lens (top gray oval) and then to the large detector array (long black line). The detector array would be movable as indicated by the arrow as to acquire images from multiple locations. In FIG. 8D the large gray half circle at the bottom represents the patient. The lines extending from the patient represent the photons emitted. The large black arc represents the collimator. The photons go through the collimator to the first lens to the second lens and then to the detector array. In FIG. 8e the large round gray circle represents the patient. The dashed lines represent the photons emitted from the body, which travel through the lens (gray oval with black line) to a mirror (angled short black line) to the second lens and then to the large detector array (long black line). In FIG. 8F the patient is shown on the gantry. The black rectangle with the gray ovals represent the collimator and lens apparatus. The angled line represents a mirror. The long black line represent the detector arrays. In this setup, two large detector arrays would be used.

Illustration of current imaging apparatus of FIG. 9A. A series of detectors surround the patient which are illustrated by dark lines on the supporting cylindrical structure. The diameter of this type structure is typically between 0.8-1.0 meters. The embodiment discussed in Alternative Implementation #1 is shown in FIG. 9B. This embodiment includes: the cylindrical supporting device, multiple lenses, and multiple large detector arrays. The lens and detector arrays are illustrated at the bottom of the figure. Note that this configuration is considerably larger—in this figure the diameter is ~3.0 meters. The lenses allow the photons to spread out over the detector arrays and, thus, improve the net resolution.

Figure 10:
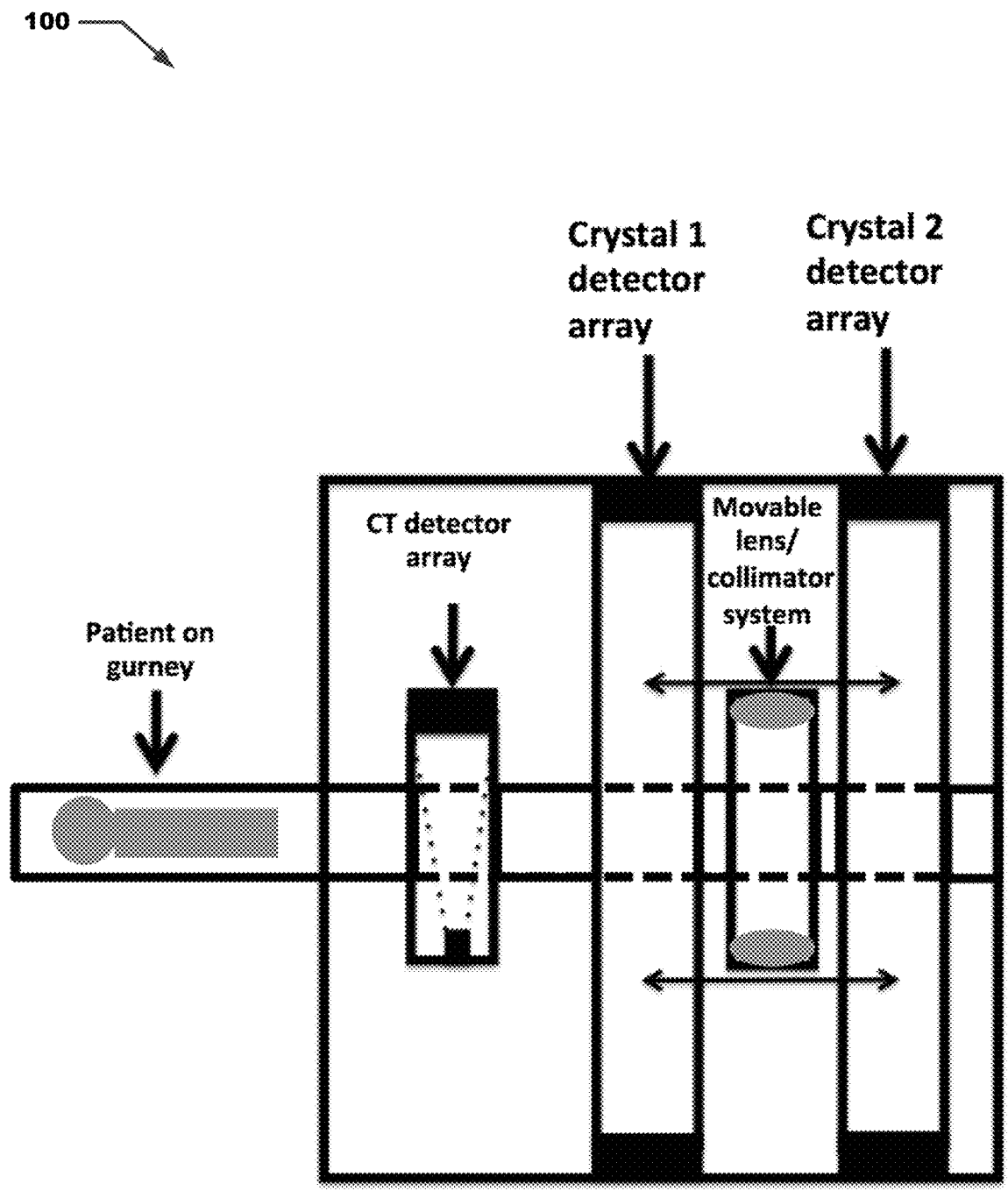
FIG. 10 is an illustration combination of CT scanner together with two different types of detector arrays: the first set consisting of crystals for detection of single photon radioactive decay and the second set of crystals for detection of dual photon positron decay.

FIG. 10 illustrates the preferred embodiment of this patent and is discussed in Alternative Implementations 7 & 8 in the Summary Section. The radiopharmaceutical dose is administered to the patient. The patient is then placed on a standard gurney allowing for translation. The patient is then brought in for the CT scan and then moved into the appropriate position for the subsequent molecular imaging scan. If the radiopharmaceutical administered decays via positron decay, it would nominally be scanned under a set of crystals (such as LSO or BGO) and could be done with or without collimation. If the radiopharmaceutical decays with single photon decay, it would nominally be scanned under the set of crystals (such as NaI). These high spatial resolution images would be fused with the CT for viewing.

Figure 12:
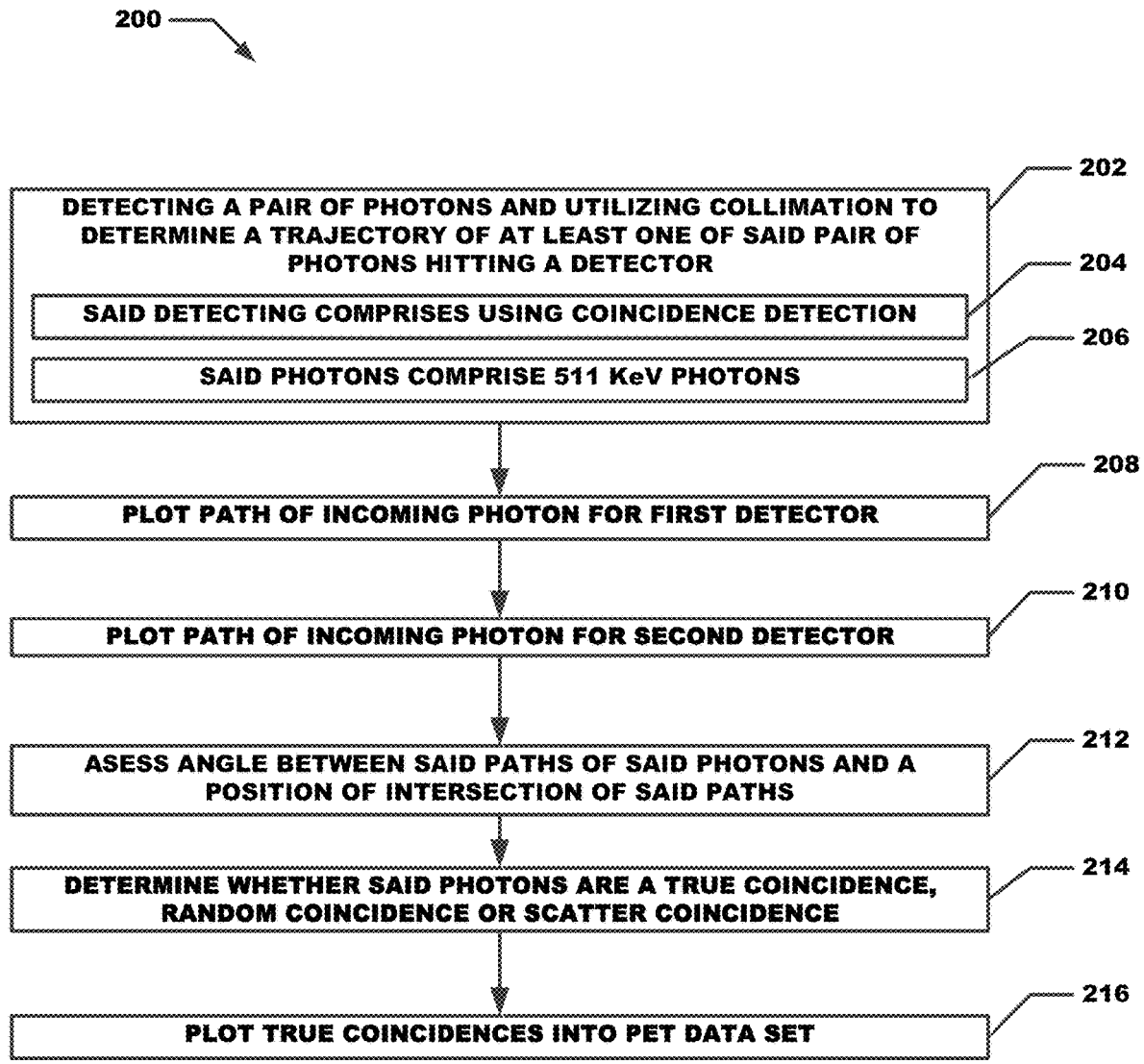
FIG. 12 is a flow diagram of a second embodiment of a method for providing improved spatial resolution of molecular and radiological imaging in accordance with embodiments of the present invention.
Figure 13:
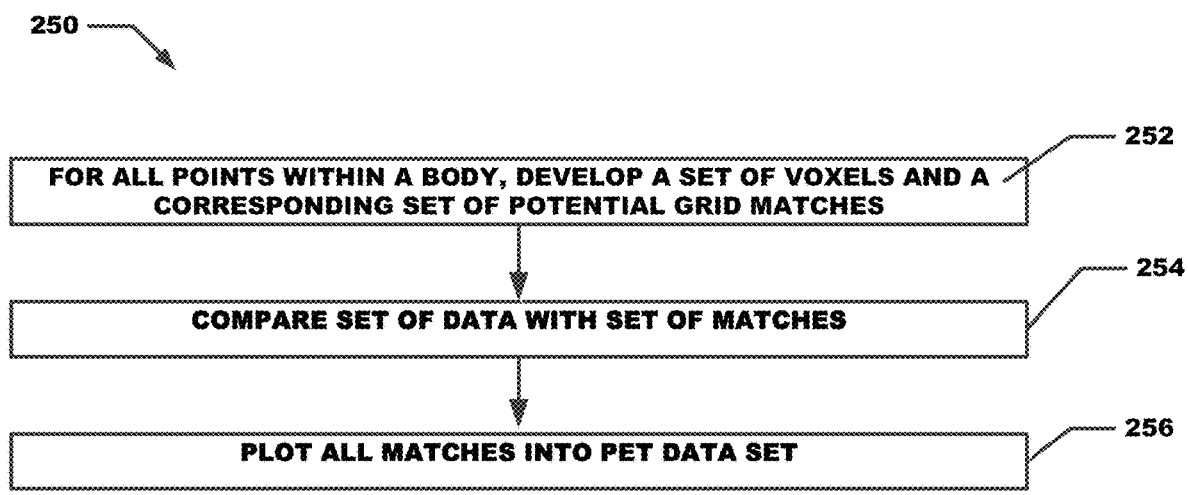
FIG. 13 is a flow diagram of a method for providing improved spatial resolution of molecular and radiological imaging in accordance with embodiments of the present invention.

A flow chart of the presently disclosed method is depicted in FIGS. 11, 12 and 13. The rectangular elements are herein denoted "processing blocks" and represent computer software instructions or groups of instructions. Alternatively, the processing represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Referring now to FIG. 11, a first method 150 is shown. Processing begins at processing block 152 which discloses plotting the detectors, lenses and patient in a single coordinate system. Processing block 154 states plotting known points on detectors based on coincidence detection. Processing block 156 recites using laws of refraction and systems of equations to solve for trajectory of a photon path. Processing block 158 recites plotting the photon paths and processing block 160 discloses plotting the resulting PET dataset.

FIG. 12 discloses a second method 200. Processing block 202 recites detecting a pair of photons and utilizing collimation to determine a trajectory of at least one of said pair of photons hitting a detector. Processing block 204 states plot path of incoming photon for first detector. Processing block 206 recites plot path of incoming photon for second detector.

Processing block 208 discloses plotting path of incoming photon for a first detector. Processing block 210 states plotting a path of incoming photon for a second detector. Processing block 212 discloses assessing an angle between said paths of said photons and a position of intersection of said paths. Processing block 214 recites determining whether said photons are a true coincidence, random coincidence or scatter coincidence. Processing block 216 states plotting true coincidences into pet data set.

Referring now to FIG. 13 a third method 250 is shown. Method 250 begins with processing block 252 which discloses for all points within a body, develop a set of voxels and a corresponding set of potential grid matches. Processing block 254 states comparing the set of data with a set of matches. Processing block 256 recites plotting all matches into a PET data set.

References to "a microprocessor" and "a processor", or "the microprocessor" and "the processor," may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor" or "processor" terminology may thus also be understood to include a central processing unit, an arithmetic logic unit, an application-specific integrated circuit (IC), and/or a task engine, with such examples provided for illustration and not limitation.

Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where such memory may be contiguous and/or partitioned based on the application. Accordingly, references to a database may be understood to include one or more memory associations, where such references may include commercially available database products (e.g., SQL, Informix, Oracle) and also proprietary databases, and may also include other structures for associating memory such as links, queues, graphs, trees, with such structures provided for illustration and not limitation.

References to a network, unless provided otherwise, may include one or more intranets and/or the internet, as well as a virtual network. References herein to microprocessor instructions or microprocessor-executable instructions, in accordance with the above, may be understood to include programmable hardware.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art.

Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD-ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

What is claimed is:

1. An apparatus for radiographic imaging used in conjunction with an x-ray tube for the detection of X-rays, the apparatus comprising:
    a collimator in a cylindrical device through which photons emitted from a radionuclide or radiopharmaceutical pass;
    a mirror used to redirect the photons, said mirror in communication with said collimator;
    a lens system through which the photons pass and are magnified and spread over a larger detector area, said lens system in communication with said collimator;
    a shutter system for selection of an angle of said photons, said shutter system in communication with said collimator;
    a detector array having a plurality of detectors wherein a first detector of said detector array abuts a second detector of said detector array, said detector array in communication with said lens system, said detector array configured to accommodate a magnified area which receives the photons; and
    a processor providing additional processing based on photon intercepts on the detector array to reduce image errors.

* * * * *